(12) United States Patent
Uchiyama

(10) Patent No.: US 8,469,879 B2
(45) Date of Patent: Jun. 25, 2013

(54) CAPSULE GUIDING SYSTEM AND CAPSULE GUIDING METHOD

(75) Inventor: Akio Uchiyama, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 628 days.

(21) Appl. No.: 12/720,142

(22) Filed: Mar. 9, 2010

(65) Prior Publication Data

US 2010/0168516 A1 Jul. 1, 2010

Related U.S. Application Data

(63) Continuation of application No. PCT/JP2008/065328, filed on Aug. 27, 2008.

(30) Foreign Application Priority Data

Sep. 11, 2007 (JP) ................................. 2007-235080

(51) Int. Cl.
*A61B 1/04* (2006.01)
(52) U.S. Cl.
USPC .............................. 600/109; 604/506; 396/17
(58) Field of Classification Search
USPC .... 600/12, 101, 109, 114, 117, 118; 604/506; 396/17
See application file for complete search history.

(56) References Cited

U.S. PATENT DOCUMENTS

| | | | | |
|---|---|---|---|---|
| 2003/0229268 A1* | 12/2003 | Uchiyama et al. | ............ | 600/109 |
| 2004/0236180 A1* | 11/2004 | Uchiyama et al. | ............ | 600/109 |
| 2005/0123179 A1* | 6/2005 | Chen et al. | ..................... | 382/128 |
| 2006/0270903 A1 | 11/2006 | Uchiyama et al. | ............ | 600/118 |
| 2007/0197869 A1 | 8/2007 | Uchiyama et al. | ............ | 600/109 |
| 2007/0197870 A1 | 8/2007 | Uchiyama et al. | ............ | 600/114 |

(Continued)

FOREIGN PATENT DOCUMENTS

| | | |
|---|---|---|
| JP | 2003-299612 | 10/2003 |
| JP | 2004-255174 | 9/2004 |
| JP | 2005-52502 A | 3/2005 |
| JP | 2006-149668 | 6/2006 |

OTHER PUBLICATIONS

Japanese Office Action dated Dec. 20, 2011 from corresponding Japanese Patent Application No. 2007-235080 together with a partial English language translation.
European Search Report dated Feb. 13, 2012 from corresponding European Patent Application No. EP 08 83 0833.3.

*Primary Examiner* — Clayton E LaBalle
*Assistant Examiner* — Warren K Fenwick
(74) *Attorney, Agent, or Firm* — Scully, Scott, Murphy & Presser, P.C.

(57) ABSTRACT

A capsule guiding system includes a capsule medical device having an imaging device that takes an in-vivo image of a subject and a magnet with a magnetization direction that is relatively fixed with respect to the imaging device; a magnetic guiding device that applies a magnetic field to the magnet in the subject and guides the capsule medical device; a display unit that displays the in-vivo image of the subject; and a control unit that causes the magnetic guiding device to apply a magnetic field in a reference direction to the magnet, initializes a rotation angle of an image taken by the imaging device when the magnetization direction of the magnet is oriented to the reference direction following the magnetic field in the reference direction, performs, referring to the image, rotation correction on subsequent in-vivo images, and causes the display unit to sequentially display the corrected in-vivo images.

12 Claims, 8 Drawing Sheets

U.S. PATENT DOCUMENTS

| | | | |
|---|---|---|---|
| 2007/0197872 A1 | 8/2007 | Uchiyama et al. | 600/117 |
| 2007/0219405 A1 | 9/2007 | Uchiyama et al. | 600/12 |
| 2007/0299301 A1 | 12/2007 | Uchiyama et al. | 600/101 |
| 2008/0249360 A1* | 10/2008 | Li et al. | 600/118 |
| 2008/0300458 A1* | 12/2008 | Kim et al. | 600/118 |
| 2010/0010304 A1* | 1/2010 | Kawano | 600/117 |
| 2010/0010305 A1* | 1/2010 | Kawano | 600/118 |
| 2010/0010306 A1* | 1/2010 | Kawano et al. | 600/118 |

* cited by examiner

CAPSULE GUIDING SYSTEM AND CAPSULE GUIDING METHOD

CROSS-REFERENCE TO RELATED APPLICATIONS

This application is a continuation of PCT international application Ser. No. PCT/JP2008/065328 filed on Aug. 27, 2008 which designates the United States, incorporated herein by reference, and which claims the benefit of priority from Japanese Patent Application No. 2007-235080, filed on Sep. 11, 2007, incorporated herein by reference.

BACKGROUND OF THE INVENTION

1. Field of the Invention

The present invention relates to a capsule guiding system and a capsule guiding method for guiding, by a magnetic force, a capsule medical device that is introduced into a subject, such as a patient.

2. Description of the Related Art

In the field of endoscopy, capsule endoscopes that can be introduced into the alimentary canal of a subject, such as a patient, have been used. A capsule endoscope is swallowed by a subject, then takes images of the internal organs of the subject (hereinafter, sometimes referred to as an in-vivo image) while moving through the alimentary canal by peristalsis, and wirelessly transmits the taken in-vivo images to a receiving device outside the subject. The capsule endoscope sequentially takes in-vivo images of the subject over a period of time until it is naturally excreted to the outside of the subject.

Capsule guiding systems for guiding (magnetic guiding) a capsule endoscope that is introduced into a subject by a magnetic force have been also proposed. Generally, in a capsule guiding system, a capsule endoscope provided with a spiral protrusion on the outer circumference of its capsule-shaped casing incorporating a magnet that is magnetized in a radial direction is introduced into the alimentary canal of a subject. By applying a rotation magnetic field that is generated by a rotation magnetic field generating device to the magnet in the capsule endoscope, the capsule endoscope and the spiral protrusion are rotated so as to generate a drive force for the capsule endoscope. Accordingly, the capsule endoscope is magnetically guided to a desired position in the subject.

Such capsule guiding systems include a system in which the magnetization direction of the magnet incorporated in the capsule endoscope and a reference plane direction of an imaging device (for example, the upper direction of a light-receiving surface) are relatively fixed. The capsule endoscope sequentially takes in-vivo images while making a rotation movement following the rotation magnetic field. The rotation of in-vivo images caused by the rotation of the capsule endoscope is corrected by image processing, and in-vivo images not rotated are sequentially displayed on a display device (see Japanese Laid-open Patent Publication No. 2003-299612 and Japanese Laid-open Patent Publication No. 2006-149668, for example).

SUMMARY OF THE INVENTION

According to an aspect of the present invention, there is provided a capsule guiding system including a capsule medical device including in a capsule casing an imaging device configured to take an in-vivo image of a subject and a magnet with a magnetization direction that is relatively fixed with respect to the imaging device; a magnetic guiding device configured to apply a magnetic field to the magnet of the capsule medical device introduced into the subject and to guide the capsule medical device with the magnetic field; a display unit configured to display the in-vivo image of the subject taken by the imaging device; and a control unit configured to cause the magnetic guiding device to apply a magnetic field in a reference direction to the magnet, configured to initialize a rotation angle of an image taken by the imaging device when the magnetization direction of the magnet is oriented to the reference direction following the magnetic field in the reference direction, configured to perform, referring to the image, rotation correction on subsequent in-vivo images, and configured to cause the display unit to sequentially display the in-vivo images on which the rotation correction is performed.

According to another aspect of the present invention, there is provided a capsule guiding method for magnetically guiding a capsule medical device that is introduced into a subject and sequentially takes in-vivo images chronologically, the capsule guiding method including acquiring information on magnetic guidance of the capsule medical device; determining whether initialization of a rotation angle of an image taken by the capsule medical device is necessary based on the information on the magnetic guidance of the capsule medical device, which is acquired at the acquiring, and condition information previously set; performing, when it is determined that the initialization of the rotation angle of the image is necessary at the determining, an initialization process on the rotation angle of the image; performing rotation correction on subsequent images taken by the capsule medical device referring to the image whose rotation angle is initialized at the initialization process step; and displaying the subsequent images on which the rotation correction is performed at the rotation correction.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A capsule guiding system and a capsule guiding method that are best modes to carry out the present invention are explained below. In the following, as an example of the capsule guiding system and the capsule guiding method according to the present invention, those in which a capsule endoscope (an example of the capsule medical device) that takes an in-vivo image of a subject is illustrated. However, the embodiment does not limit the present invention.

Embodiment

Figure 1:
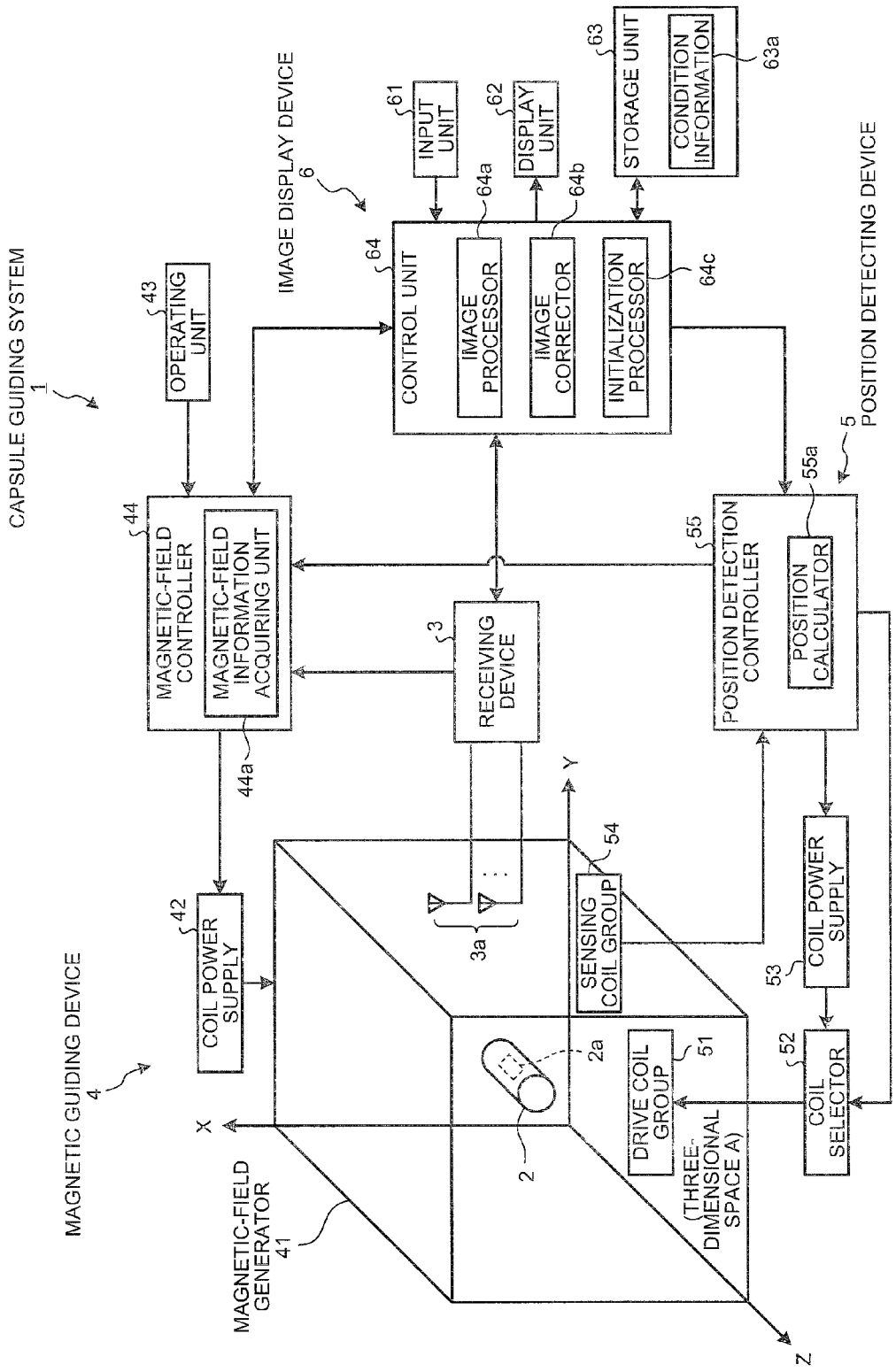
FIG. 1 is a block diagram schematically illustrating a configuration example of a capsule guiding system according to an embodiment of the present invention.

FIG. 1 is a block diagram schematically illustrating a configuration example of the capsule guiding system according to the embodiment of the present invention. As illustrated in FIG. 1, a capsule guiding system 1 according to the embodiment includes a capsule endoscope 2 that takes an in-vivo image of a subject; a receiving device 3 that receives the in-vivo image from the capsule endoscope 2; a magnetic guiding device 4 that magnetically guides the capsule endoscope 2 that is introduced into the subject; a position detecting device 5 that detects the position and direction of the capsule endoscope 2 in the subject; and an image display device 6 that displays in-vivo images taken by the capsule endoscope 2.

The capsule endoscope 2 is an example of a capsule medical device that is introduced into the internal organ of a subject. The capsule endoscope 2 takes in-vivo images of the subject as subject in-vivo information. Specifically, the capsule endoscope 2 has an imaging function and a wireless communication function in its capsule-shaped casing. After being introduced into the alimentary canal of the subject (not shown) such as a patient, the capsule endoscope 2 sequentially takes in-vivo images while moving through the alimentary canal of the subject. The capsule endoscope 2 sequentially transmits wireless signals including the in-vivo images of the subject to the receiving device 3 outside the subject. The capsule endoscope 2 incorporates a magnetic member, such as a permanent magnet, or an electromagnet (hereinafter, simply referred to as a magnet), and is magnetically guided by a magnetic field that is formed by the magnetic guiding device 4. The capsule endoscope 2 includes in the capsule-shaped casing an LC marker 2a, which is an LC resonating circuit formed of a coil and a capacitor. The position detecting device 5 (specifically, a drive coil group 51 described below) applies a magnetic field to the LC marker 2a and the LC marker 2a emits an induced magnetic field due to the applied magnetic field. The induced magnetic field emitted by the LC marker 2a is detected by the position detecting device 5 (specifically, a sensing coil group 54 described below).

The receiving device 3 includes a plurality of receiving antennas 3a, and receives in-vivo images of the subject from the capsule endoscope 2 via the receiving antennas 3a. Specifically, the receiving antennas 3a are discretely arranged on the body surface of the subject with the alimentary canal to which the capsule endoscope 2 is introduced, and capture wireless signals from the capsule endoscope 2 that moves (or magnetically guided) along the alimentary canal. The receiving device 3 receives wireless signals from the capsule endoscope 2 via the receiving antennas 3a. The receiving device 3 performs a predetermined demodulating process on the wireless signal and extracts an image signal included in the wireless signal. The image signal extracted by the receiving device 3 is a signal including the in-vivo image taken by the capsule endoscope 2. The receiving device 3 records in its recording medium the in-vivo image and transmits an image signal of the in-vivo image to the image display device 6 (specifically, to a control unit 64) at the timing at which the receiving device 3 receives information of an instruction for transmitting an image from the control unit 64 of the image display device 6 described below. The receiving device 3 transmits a synchronizing signal to the control unit 64 of the image display device 6 and a magnetic-field controller 44 (described below) of the magnetic guiding device 4 at the timing at which a predetermined time has passed since the capsule endoscope 2 took an in-vivo image (or since the in-vivo image is received from the capsule endoscope 2). The synchronizing signal is used to synchronize the magnetic-field controller 44 and the control unit 64 of the image display device 6.

The magnetic guiding device 4 magnetically guides the capsule endoscope 2 as described above. The magnetic guiding device 4 includes a magnetic-field generator 41 that generates a magnetic-field for guiding the capsule endoscope 2 within the subject; a coil power supply 42 for supplying electric current to the coil (electromagnet) of the magnetic-field generator 41; an operating unit 43 for operating magnetic guidance of the capsule endoscope 2; and the magnetic-field controller 44 that controls the intensity and direction of a magnetic field generated by the magnetic-field generator 41.

The magnetic-field generator 41 is constructed by combining a plurality of electromagnets such as Helmholtz coils, and generates a magnetic field that enables guidance of the capsule endoscope 2 in the subject. Specifically, the magnetic-field generator 41 has a defined three-axis orthogonal coordinate system (hereinafter, referred to as absolute coordinates) of orthogonal three axes (X-axis, Y-axis, and Z-axis) and generates magnetic fields with desired intensities in the respective directions (the X-axis direction, Y-axis direction, and Z-axis direction) of the absolute coordinate system. The magnetic-field generator 41 forms in a three-dimensional space A of the absolute coordinate system (i.e., in the space surrounded by the electromagnets of the magnetic-field generator 41) a three-dimensional rotation magnetic field, or a three-dimensional gradient magnetic field, that is formed of magnetic fields in the respective axis directions of the absolute coordinate system. The magnetic-field generator 41 applies the rotation magnetic field or the gradient magnetic field to the magnet (a magnet 29 described below) in the capsule endoscope 2 positioned in the subject (not shown) on a bed that has been moved into the three-dimensional space A. The magnetic-field generator 41 magnetically guides the capsule endoscope 2 by the rotation magnetic field or the gradient magnetic field. The magnetic-field generator 41 generates in the three-dimensional space A a magnetic field in a predetermined reference direction for causing the magnet in the capsule endoscope 2 to follow the magnetic field. This forcibly changes the magnetization direction of the magnet in the capsule endoscope 2 to the reference direction. The magnetic fields in the axis directions of the absolute coordinate system (i.e., the rotation magnetic field, the gradient magnetic field, and the magnetic field in the reference direction) generated by the magnetic-field generator 41 are controlled by an AC current (the amount of power from the coil power supply 42) supplied from the coil power supply 42.

The absolute coordinate system may be a three-dimensional orthogonal coordinate system defined with respect to the magnetic-field generator 41 (i.e., fixed with respect to the magnetic-field generator 41) as described above. Alternatively, it may be a three-axis orthogonal coordinate system fixed with respect to the subject (not shown) that has the capsule endoscope 2 in his/her alimentary canal or a three-axis orthogonal coordinate system fixed with respect to the bed (not shown) on which the subject is laid.

The coil power supply 42 supplies to the magnetic-field generator 41 an electric current for generating a magnetic field to be applied to the capsule endoscope 2 in the subject. The coil power supply 42 includes a plurality of power supplies corresponding to a plurality of coils (not shown) that form the magnetic-field generator 41, and supplies an AC to each coil of the magnetic-field generator 41 to generate a magnetic field in each axis direction of the above-described absolute coordinate system under the control of the magnetic-field controller 44.

The operating unit 43 is constructed using an input device such as a lever or an input button. In response to an input operation by a user such as a doctor or a nurse, the operating unit 43 inputs instruction information of an instruction for magnetically guiding the capsule endoscope 2 to the magnetic-field controller 44.

Based on the instruction information input by the operating unit 43, the magnetic-field controller 44 controls the amount of electric current from the coil power supply 42 to the magnetic-field generator 41 and controls, via the control of the coil power supply 42, a magnetic-field generating operation of the magnetic-field generator 41 that generates the above-described rotation magnetic field or the gradient magnetic field. In this case, the magnetic-field controller 44 acquires the current position information (hereinafter, referred to as capsule position information) and the current direction information (hereinafter, referred to as capsule direction information) on the capsule endoscope 2 in the subject from a position detection controller 55 of the position detecting device 5 described below. The magnetic-field controller 44 determines the intensity and direction of a magnetic field applied to the capsule endoscope 2 based on the acquired capsule position information and the capsule direction information. The magnetic-field controller 44 causes the magnetic-field generator 41 to emit a magnetic field with an intensity and a direction for achieving magnetic guidance of the capsule endoscope 2, which is instructed by the instruction information from the operating unit 43, at the current position of the capsule endoscope 2 in the subject. As a result, the magnetic-field controller 44 controls magnetic guidance the capsule endoscope 2 to a desired position or a desired direction in the subject.

The magnetic-field controller 44 includes a magnetic-field information acquiring unit 44a. At the timing at which a synchronizing signal is acquired from the receiving device 3, the magnetic-field information acquiring unit 44a acquires as magnetic-field intensity information and magnetic-field direction information the intensity and direction of a magnetic field that is applied to the capsule endoscope 2 in the three-dimensional space A (specifically, in the subject) by the magnetic-field generator 41. In this case, at the timing at which the magnetic-field information acquiring unit 44a acquires the synchronizing signal, the magnetic-field information acquiring unit 44a acquires the magnetic-field intensity information and the magnetic-field direction information at this timing based on an AC that is supplied by the coil power supply 42 to the magnetic-field generator 41. At the timing at which the magnetic-field information acquiring unit 44a acquires the synchronizing signal, the magnetic-field information acquiring unit 44a acquires the capsule position information and the capsule direction information from the position detecting device 5. The magnetic-field information acquiring unit 44a stores the acquired magnetic-field intensity information, magnetic-field direction information, the capsule position information, and the capsule direction information. The magnetic-field information acquiring unit 44a transmits to the control unit 64 the magnetic-field intensity information, the magnetic-field direction information, the capsule position information, and the capsule direction information at the timing at which the control unit 64 of the image display device 6 described below issues an instruction for transmitting the information.

As described above, the position detecting device 5 detects the position and direction of the capsule endoscope 2 in the subject positioned in the three-dimensional space A. The position detecting device 5 includes the drive coil group 51 that applies a magnetic field to the LC marker 2a in the capsule endoscope 2; a coil selector 52 that selects a drive coil for generating a magnetic field from the drive coil group 51; a coil power supply 53 that supplies an electric current to the drive coil selected by the coil selector 52; the sensing coil group 54 that detects an induced magnetic field emitted by the LC marker 2a; and the position detection controller 55 that controls each component of the position detecting device 5 and acquires the capsule position information and the capsule direction information.

The drive coil group 51 is constructed using a plurality of drive coils that generate a magnetic field for detecting the current position and the current direction of the capsule endoscope 2 in the subject. The drive coil group 51 applies a magnetic field with an intensity and a direction that are optimum for the current position and the coil axis direction of the LC marker 2a in the three-dimensional space A to the LC marker 2a so as to cause the LC marker 2a to emit an induced magnetic field due to the influence of the applied magnetic field.

The coil selector 52 selects a drive coil for generating a magnetic field from the drive coil group 51 under the control of the position detection controller 55. One or more drive coils selected by the coil selector 52 generate, at the current position of the LC marker 2a in the three-dimensional space A, a magnetic field with an intensity and a direction that are optimum as a magnetic field passing through the LC marker 2a in the coil axis direction.

The coil power supply 53 includes a plurality of power supplies corresponding to the number of drive coils of the drive coil group 51, and supplies an AC to one or more drive coils selected by the coil selector 52 from the drive coil group 51 under the control of the position detection controller 55. In this case, the AC signal generated by the coil power supply 53 is applied to one or more drive coils selected from the drive coil group 51 via the coil selector 52 to cause one or more drive coils to generate a magnetic field.

The sensing coil group 54 is constructed using a plurality of sensing coils to detect a magnetic field in order to detect the current position and the current direction of the capsule endoscope 2 in the subject. Specifically, the sensing coil group 54 detects an induced magnetic field emitted by the LC marker 2a due to the magnetic field from the drive coil group 51. The sensing coil group 54 sends a detection result on the induced magnetic field detected from the LC marker 2a to the position detection controller 55.

The position detection controller 55 controls the drive coil group 51, the coil selector 52, the coil power supply 53, and the sensing coil group 54 when detecting the current position and the current direction of the capsule endoscope 2 in the subject. Specifically, under the control of the control unit 64 of the image display device 6 described below, the position detection controller 55 causes the coil selector 52 to select one or more drive coils from the drive coil group 51, controls the amount of electric current from the coil power supply 53 to one or more drive coils selected by the coil selector 52, and controls the magnetic-field generating operation of the drive coil group 51 via the control on the amount of electric current. The position detection controller 55 controls input/output of the signal from the sensing coil group 54, and acquires a result of detecting the induced magnetic field from the LC marker 2a, which is detected by the sensing coil group 54.

The position detection controller 55 includes a position calculator 55a. Based on the result of detecting the induced magnetic filed from the LC marker 2a, which is acquired from the sensing coil group 54, the position calculator 55a calculates the capsule position information (current position coordinates in the three dimensional space A) and the capsule direction information (a direction vector representing the current direction of the capsule endoscope 2 in the three-dimensional space A) on the capsule endoscope 2 in the subject. The position detection controller 55 sends the capsule position information and the capsule direction information to the magnetic-field controller 44 under the control of the control unit 64 of the image display device 6.

The image display device 6 displays an in-vivo image of the subject, which is taken by the capsule endoscope 2, as described above. The image display device 6 includes an input unit 61 that inputs various types of information; a display unit 62 that displays information on in-vivo images; a storage unit 63 that stores various types of information such as an in-vivo image of the subject; and the control unit 64 that controls each component of the image display device 6.

The input unit 61 is constructed using an input device such as a keyboard and a mouse, and inputs various types of information to the control unit 64 in response to an input operation by a user such as a doctor or a nurse. The various types of information input by the input unit 61 to the control unit 64 include instruction information of an instruction to the control unit 64, patient information on the subject, and examination information on the subject. The patient information on the subject is identification information that identifies the subject, and includes, for example, the patient name, patient ID, birth date, sex, and age of the subject. The examination information on the subject is the identification information that identifies capsule endoscope examination (examination in which the capsule endoscope 2 is introduced into the alimentary canal to observe the inside of the alimentary canal), which is carried out on the subject, and includes, for example, the examination ID and the examination date.

The display unit 62 can be constructed by various types of displays such as a CRT display or a liquid crystal display, and displays various types of information for which the control unit 64 issues a display instruction. Specifically, the display unit 62 displays information useful for a capsule endoscope examination, such as an in-vivo image group of the subject, which are taken by the capsule endoscope 2, the patient information on the subject, and examination information on the subject. The display unit 62 also displays information useful for magnetically guiding the capsule endoscope 2, such as the capsule position information and the capsule direction information at the time when the capsule endoscope 2 takes the currently-displayed in-vivo image of the subject and information on a magnetic field applied to the magnet in the capsule endoscope 2 (magnetic-field intensity information and magnetic-field direction information). While observing the in-vivo image of the subject displayed on the display unit 62, a user such as a doctor or a nurse operates the magnetic guidance of the capsule endoscope 2 with reference to the various types of information on the display unit 62.

The storage unit 63 can be constructed by various types of storage media for storing information such that the information is rewritable, such as a RAM, an EEPROM, a flash memory, or a hard disk. The storage unit 63 stores various types of information for which the control unit 64 issues a storing instruction, and sends to the control unit 64 the information from the stored various types of information for which the control unit 64 issues a reading instruction. Under the control of the control unit 64, the storage unit 63 stores a group of in-vivo images of the subject, the patient information on the subject, the examination information on the subject, the capsule position information, the capsule direction information, the magnetic-field intensity information, and the magnetic-field direction information. The storage unit 63 stores a reference direction of a rotation angle of an in-vivo image, a reference plane direction that is defined for the display unit 62, and an image plane direction defined for each in-vivo image. The storage unit 63 previously stores condition information 63a on the necessity for initializing a rotation angle of an in-vivo image. The condition information 63a includes various types of thresholds for determining whether it is necessary to perform an initializing process on an image rotation angle described below (for example, a threshold concerning the capsule position information and a threshold concerning the capsule direction information).

The control unit 64 controls operations of the respective components of the image display device 6 (the input unit 61, the display unit 62, and the storage unit 63) and controls an input/output of a signal between the components. Specifically, based on the instruction information input by the input unit 61, the control unit 64 causes the display unit 62 to display various types of information such as the in-vivo images, causes the storage unit 63 to store various types of information such as the in-vivo images, or causes the storage unit 63 to read the stored information.

The control unit 64 controls the position detection controller 55 to cause the position detecting device 5 to detect the capsule position information and the capsule direction information. At the timing when the control unit 64 receives a synchronizing signal from the receiving device 3, it causes the capsule position information and the capsule direction information detected by the position detecting device 5 to be transmitted from the position detection controller 55 to the magnetic-field controller 44. At the timing when a predetermined time has passed since the control unit 64 received the synchronizing signal from the receiving device 3, the control unit 64 transmits information for transmitting an image signal to the receiving device 3, and acquires the image signal from the receiving device 3. The control unit 64 includes an image processor 64a. Based on the image signal acquired from the receiving device 3, the image processor 64a generates an in-vivo image of the subject, which is taken by the capsule endoscope 2. The control unit 64 transmits to the magnetic-field controller 44 instruction information for information transmission, and, at this timing, acquires from the magnetic-field controller 44 the capsule position information, the capsule direction information, the magnetic-field intensity information, and the magnetic-field direction information at the time when the capsule endoscope 2 takes the in-vivo image acquired from the receiving device 3. The control unit 64 combines the in-vivo image (i.e., the in-vivo image generated by the image processor 64a) acquired from the receiving device 3 and the information on the magnetic guidance of the capsule endoscope 2 (i.e., the capsule position information, the capsule direction information, the magnetic-field intensity information, and the magnetic-field direction information) acquired from the magnetic-field controller 44. The in-vivo image, the capsule position information, the capsule direction information, the magnetic-field intensity information, and the magnetic-field direction information, which are combined by the control unit 64, are stored in the storage unit 63 and displayed on the display unit 62 under the control of the control unit 64.

Furthermore, the control unit 64 includes an image corrector 64b and an initialization processor 64c, and controls the magnetic-field controller 44 such that the magnetic-field generator 41 applies a magnetic field in the reference direction to the magnet (the magnet 29 described below) in the capsule endoscope 2. The image corrector 64b performs rotation correction on each image that is rotated in accordance with the rotation movement of the capsule endoscope 2 that is magnetically guided by the magnetic guiding device 4. The initialization processor 64c initializes the rotation angle of the in-vivo image that is rotated along the rotation movement of the capsule endoscope 2 (hereinafter, sometimes referred to as an image rotation angle) to a predetermined angle.

Specifically, the initialization processor 64c determines whether initialization of image rotation angle is necessary, using the condition information 63a in the storage unit 63. When the initialization processor 64c determines that the initialization is necessary, the initialization processor 64c initializes the image rotation angle of the in-vivo image (for example, it is set to 0). Alternatively, the initialization processor 64c initializes the image rotation angle of the in-vivo image based on instruction information input by the input unit 61. The image corrector 64b calculates an image rotation angle that is formed by the image whose image rotation angle is initialized by the initialization processor 64c (reference image) and an in-vivo image subsequent to the reference image, and performs rotation correction on the subsequent in-vivo image such that the calculated image rotation angle is 0. Each subsequent in-vivo image whose image rotation angle with respect to the reference image is corrected by the image corrector 64b is in the state where it is not rotated with respect to the reference image. The control unit 64 causes the display unit 62 to sequentially display in-vivo images on which the rotation correction is performed by the image corrector 64b.

Figure 2:
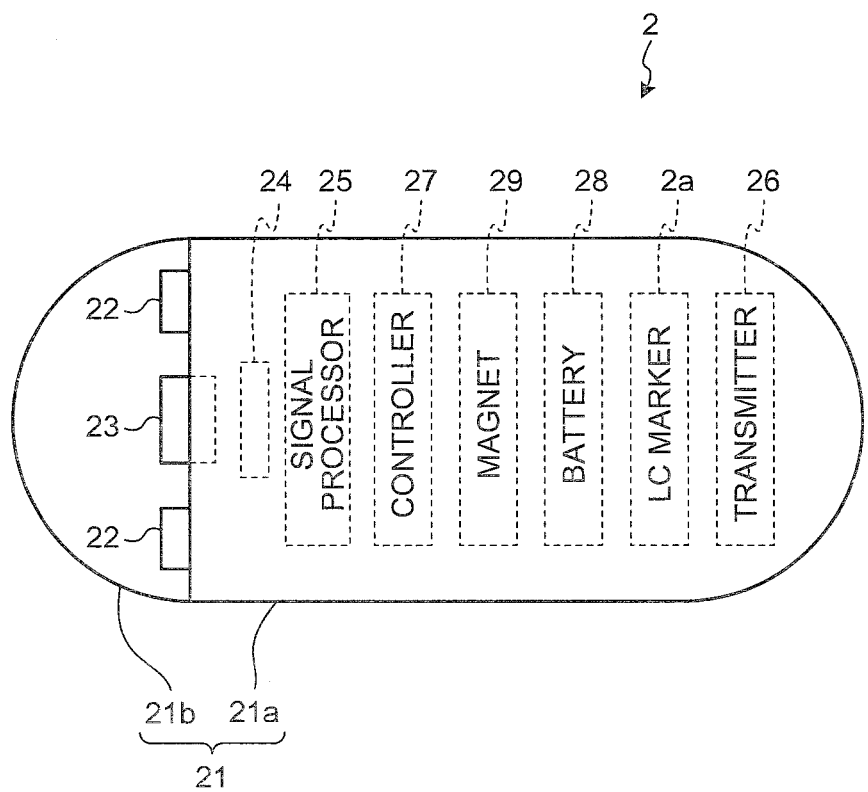
FIG. 2 is a schematic diagram illustrating a configuration example of a capsule endoscope used in the capsule guiding system according to the embodiment of the present invention.

Subsequently, the capsule endoscope 2 is explained in detail below. FIG. 2 is schematic diagram illustrating a configuration example of the capsule endoscope 2 used in the capsule guiding system 1 according to the embodiment of the present invention. As illustrated in FIG. 2, the capsule endoscope 2 includes a capsule-shaped casing 21 formed of a nearly non-transparent cylindrical casing 21a and a transparent dome-shaped casing 21b. The capsule-shaped casing 21 is formed in a way that one end (open end) of the cylindrical casing 21a whose other end is dome-shaped is closed with the dome-shaped casing 21b.

In the capsule-shaped casing 21, the LC marker 2a, an illuminating unit 22, a condenser lens 23, an imaging device 24, a signal processor 25, a transmitter 26, a controller 27, a battery 28, and the magnet 29 are housed. Specifically, the illuminating unit 22, the condenser lens 23, and the imaging device 24 are arranged on the side of the dome-shaped casing 21b, and the LC marker 2a, the signal processor 25, the transmitter 26, the controller 27, the battery 28, and the magnet 29 are arranged on the side of the cylindrical casing 21a. In this case, the imaging device 24 is fixedly arranged on the capsule-shaped casing 21, and the magnet 29 is fixedly arranged on the capsule-shaped casing 21 such that the magnet has a magnetization direction relatively fixed with respect to the imaging device 24.

The illuminating unit 22 is constructed using a light emitting device such as an LED, and illuminates an imaging field of the imaging device 24. The condenser lens 23 focuses a reflected light from an illuminated object on a light receiving surface of the imaging device 24 to form an optical image of the object on the imaging device 24. The imaging device 24 receives the reflected light from the object, which is focused by the condenser lens 23, and takes an image of the object, i.e., an in-vivo image of the subject. The signal processor 25 generates an image signal of the in-vivo image based on an output signal from the imaging device 24. The transmitter 26 performs a predetermined modulating process on the image signal, generates a wireless signal that includes the in-vivo image, and transmits the generated wireless signal to the outside (specifically, to the receiving device 3). The controller 27 controls each operation of the illuminating unit 22, the imaging device 24, the signal processor 25, and the transmitter 26. The battery 28 supplies a drive power to the illuminating unit 22, the imaging device 24, the signal processor 25, the transmitter 26, and the controller 27.

The magnet 29 is magnetized in the direction that is fixed with respect to the capsule-shaped casing 21 (for example, the radial direction of the capsule-shaped casing 21) and moves following the magnetic field that is applied by the magnetic-field generator 41. The capsule-shaped casing 21 makes the rotation movement or a displacement movement following the movement of the magnet 29. Accordingly, the capsule endoscope 2 is magnetically guided by the magnetic field from the magnetic-field generator 41.

Figure 3:
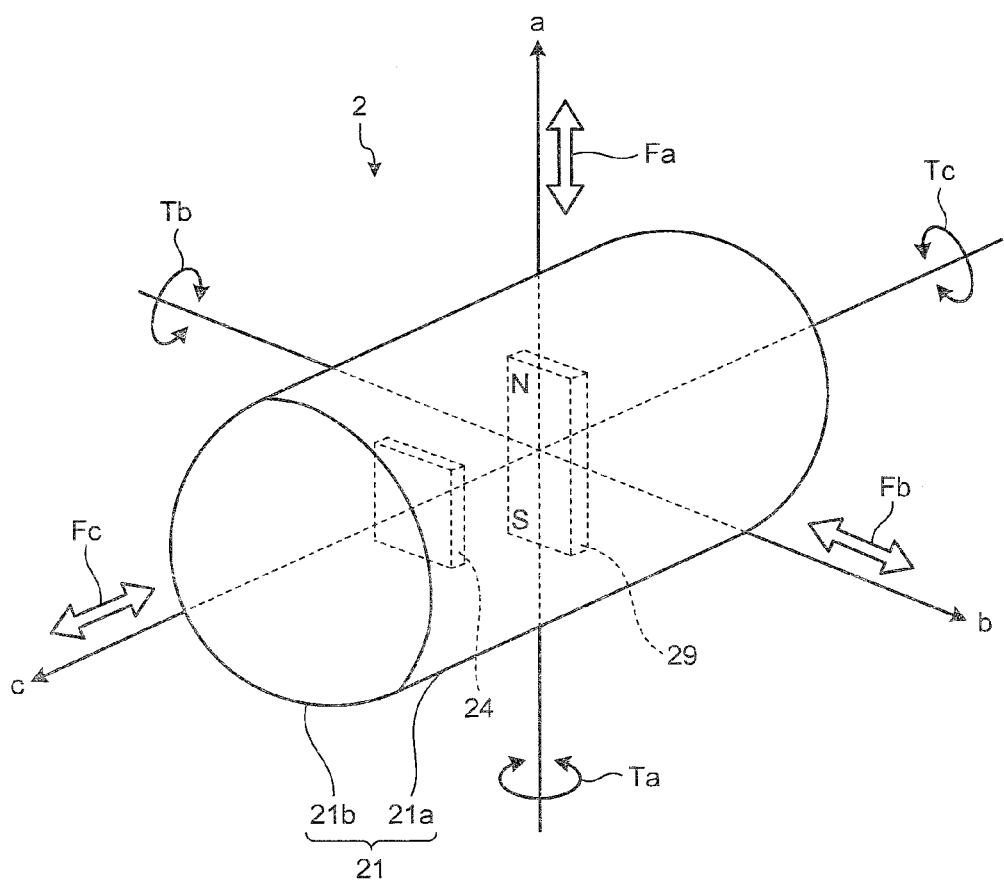
FIG. 3 is a schematic diagram illustrating a state in which an imaging device and a magnet are relatively fixedly arranged in a capsule-shaped casing.

The imaging device 24 and the magnet 29 that are relatively fixedly arranged in the capsule-shaped casing 21 are explained below. FIG. 3 is a schematic diagram illustrating the state where the imaging device 24 and the magnet 29 are relatively fixedly arranged in the capsule-shaped casing 21. As illustrated in FIG. 3, the imaging device 24 is fixedly arranged in the capsule-shaped casing 21 on the side of the dome-shaped casing 21b with respect to the center position of the capsule-shaped casing 21.

The magnet 29 is fixedly arranged in the capsule-shaped casing 21 on the side of the cylindrical casing 21a with respect to the imaging device 24. Specifically, the magnet 29 is fixedly arranged such that it is magnetized in the radial direction of the capsule-shaped casing 21 at nearly the center position of the capsule-shaped casing 21. In this case, the magnetic poles (the N pole and the S pole) of the magnet 29 are arranged in the direction orthogonal to the center axis of the longitudinal direction of the capsule-shaped casing 21 (hereinafter, longitudinal axis c), i.e., in the center axis of the radial direction of the capsule-shaped casing 21 (hereinafter, a radial direction axis a). The magnetization direction of the magnet 29 (the positive direction of the radial direction axis a illustrated in FIG. 3) coincides with a reference plane direction on the light receiving surface of the imaging device 24 (for example, the upper direction of the imaging device 24). The optical axis of the imaging device 24 nearly coincides with the longitudinal axis c of the capsule-shaped casing 21. The light receiving surface of the imaging device 24 is nearly parallel to an orthogonal two-axis plane defined by the radial direction axis a and a radial direction axis b, which is a center axis in the radial direction of the capsule-shaped casing 21 and is orthogonal to the longitudinal axis c and the radial direction a.

When a gradient magnetic field is applied in the direction of the radial direction axis a due to the magnetic field from the magnetic-field generator 41, the magnet 29 fixedly arranged in the capsule-shaped casing 21 generates a drive force Fa for driving the capsule endoscope 2 in the direction of the radial direction axis a. When a gradient magnetic field is applied in the direction of the radial direction axis b due to the magnetic field from the magnetic-field generator 41, the magnet 29 generates a drive force Fb for driving the capsule endoscope 2 in the direction of the radial direction axis b. When a gradient magnetic field is applied in the direction of the longitudinal axis c due to the magnetic field from the magnetic-field generator 41, the magnet 29 generates a drive force Fc for driving the capsule endoscope 2 in the direction of the longitudinal axis c. When a rotation magnetic field is applied on the radial direction axis a due to a magnetic field from the magnetic-field generator 41, the magnet 29 generates a rotation force Ta for causing the capsule endoscope 2 to make rotation movement on the radial direction axis a. When a rotation magnetic field is applied on the radial direction axis b due to a magnetic field from the magnetic-field generator 41, the magnet 29 generates a rotation force Tb for causing the capsule endoscope 2 to make rotation movement on the radial direction axis b. When a rotation magnetic field is applied on the longitudinal axis c of the capsule endoscope 2 due to a magnetic field from the magnetic-field generator 41, the magnet 29 generates a rotation force Tc for causing the capsule endoscope 2 to make rotation movement on the longitudinal axis c.

The capsule endoscope 2 in which the magnet 29 is fixedly arranged in the capsule-shaped casing 21 makes six-freedom-degree movement in the absolute coordinate system due to an effect of at least one of the drive forces Fa, Fb, and Fc and the rotation forces Ta, Tb, and Tc generated due to the magnetic field from the magnetic-field generator 41. The six-freedom-degree movement is a general name of the X-axis direction driving movement leading to displacement in the positive or negative direction of the X-axis, the Y-axis direction driving movement leading to displacement in the positive or negative direction of the Y-axis, the Z-axis-direction driving movement leading to displacement in the positive or negative direction of the Z-axis, the X-axis rotation movement of rotation on the X-axis, the Y-axis rotation movement of rotation on the Y-axis, and the Z-axis rotation movement of rotation on the Z-axis. The capsule endoscope 2 is magnetically guided to a desired position or a desired direction by making at least one of the six-freedom-degree movement following the magnetic field from the magnetic-field generator 41.

Figure 4:
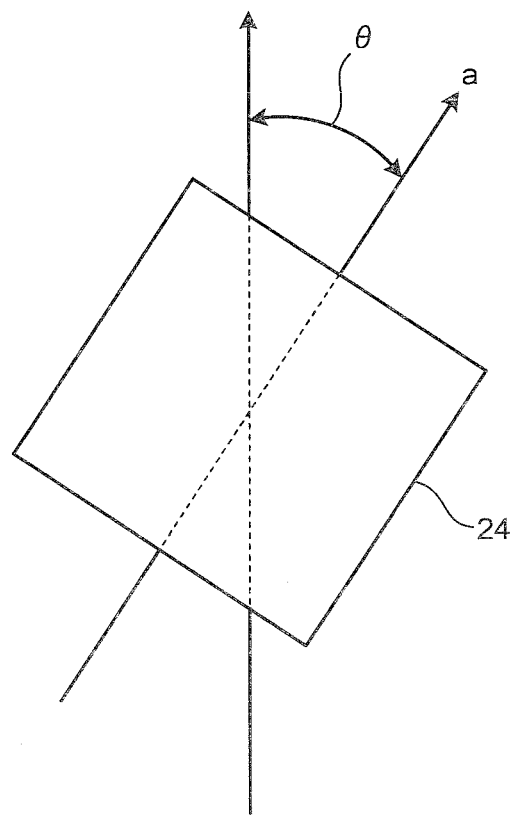
FIG. 4 is a schematic diagram explaining an image rotation angle.

The imaging device 24 having the light receiving surface whose reference direction is relatively fixed with respect to the magnetization direction of the magnet 29 (the positive direction of the radial direction axis a illustrated in FIG. 3) rotates its light receiving surface on the longitudinal axis c along with the rotation movement of the magnet 29 on the longitudinal axis c following the rotation magnetic field from the magnetic-field generator 41. In this case, a reference plane direction of an image taken by the imaging device 24 (hereinafter, image plane direction) coincides with the reference plane direction of the light receiving surface of the imaging device 24, i.e., the positive direction of the radial direction axis a, and is rotated on the longitudinal axis c along with the rotation movement on the longitudinal axis c of the magnet 29 (i.e., the rotation movement on the longitudinal axis c of the capsule endoscope 2). The image plane direction of an in-vivo image taken by the imaging device 24 being rotating forms an image rotation angle $\theta$ with respect to the image plane direction of the reference image, which is previously taken by the imaging device 24 (the image whose image rotation angle is initialized by the initialization processor 64c). As illustrated in FIG. 4, the image rotation angle $\theta$ is an angle formed by the reference direction D1 corresponding to the image plane direction of the reference image and the radial direction axis a that coincides with the reference plane direction of the imaging device 24.

The image taken by the imaging device 24 when the magnet 29 is magnetized in the reference direction in accordance with the magnetic field in the reference direction (i.e., the reference direction of the magnetic field and the magnetization direction of the magnet 29 are made coincide with each other due to the magnetic force) is a reference image for the image rotation angle $\theta$ illustrated in FIG. 4, and the image rotation angle of the reference image is initialized by the initialization processor 64c. In this case, the initialization processor 64c sets the image plane direction of the reference image to the reference direction D1 of the image rotation angle $\theta$. The image corrector 64b performs the rotation correction process on each in-vivo image such that the rotation angle $\theta$ formed by the reference direction D1 and the image plane direction of each in-vivo image is zero.

Figure 5:
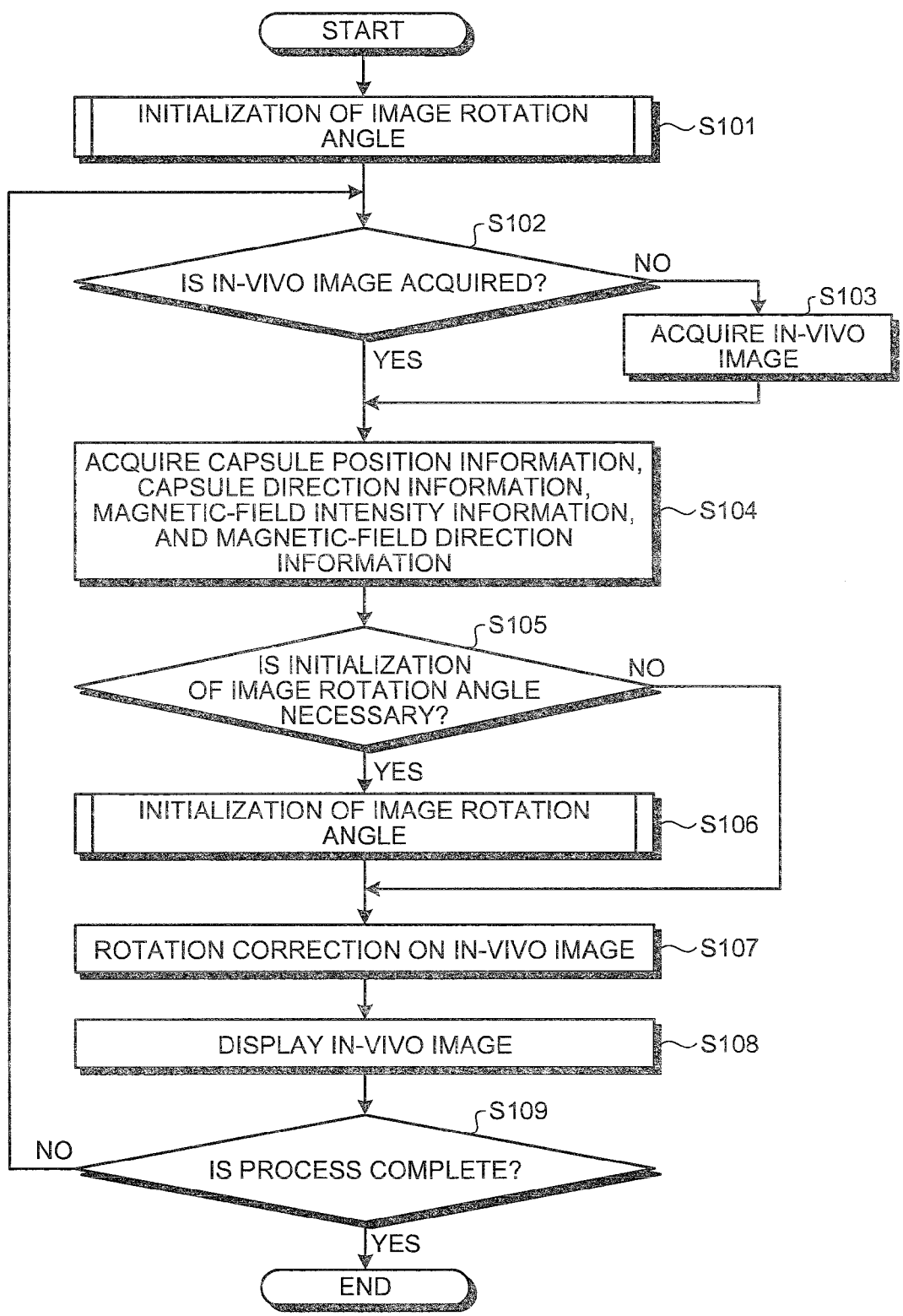
FIG. 5 is a flowchart illustrating a process procedure of a control unit of an image display device that displays an in-vivo image on which rotation correction is performed referring to an image whose image rotation angle is initialized.

Subsequently, the operations of the image display device 6 of the capsule guiding system 1 according to the embodiment of the present invention and the capsule guiding method according to the present invention are explained. FIG. 5 is a flowchart illustrating a process procedure of the control unit 64 of the image display device 6 that displays an in-vivo image on which the rotation correction is performed referring to the image whose image rotation angle is initialized.

In the capsule guiding system 1 according to the embodiment of the present invention, the capsule endoscope 2 is introduced into a subject after it is confirmed that the capsule endoscope 2 operates normally. The subject who has the capsule endoscope in his/her body is arranged in the internal space of the magnetic-field generator 41 (in the three-dimensional space A of the absolute coordinate system) while being laid on the bed. In this state, the position detecting device 5 detects the capsule position information and the capsule direction information in the subject. A user, such as a doctor or a nurse, confirms that the capsule endoscope 2 reaches a target position in the subject based on the capsule position information and the capsule direction information displayed on the display unit 62. Based on that the in-vivo image is displayed on the display unit 62, the user confirms that the capsule endoscope 2 in the subject takes in-vivo images normally. In this case, the user operates the input unit 61 of the image display device 6 to input instruction information of an instruction for initializing the image rotation angle.

In this state, the control unit 64 of the image display device 6 controls the magnetic guiding device 4 to apply a magnetic field in the reference direction to the magnet 29 of the capsule endoscope 2 in the subject, initializes the image rotation angle of the reference image, which is taken by the imaging device 24 of the capsule endoscope 2 when the magnet 29 is magnetized in the reference direction following the magnetic field in the reference direction, performs, referring to the image, the rotation correcting process on the in-vivo image, and causes the display unit 62 to display the in-vivo image on which the rotation correcting process is performed.

Specifically, as illustrated in FIG. 5, the control unit 64 first performs the initializing process on the image rotation angle based on instruction information input by the input unit 61 (step S101). Subsequently, the control unit 64 determines whether the in-vivo image taken by the capsule endoscope 2 is acquired (step S102). At step S102, the control unit 64 transmits information of an instruction for transmitting an image signal to the receiving device 3 and, and, when an image signal of an in-vivo image is acquired from the receiving device 3, determines that the in-vivo image is acquired (YES at step S102). Thereafter, the control unit 64 transmits information of an instruction for information transmission to the magnetic-field controller 44 and acquires from the magnetic-field controller 44 information on magnetic guidance of the capsule endoscope 2, i.e., the capsule position information, the capsule direction information, the magnetic-field intensity information, and the magnetic-field direction information (step S104). The control unit 64 stores in the storage unit 63 the capsule position information, the capsule direction information, the magnetic-field intensity information, and the magnetic-field direction information in association with the in-vivo image.

Subsequently, the control unit 64 determines whether initialization of the image rotation angle is necessary at the current moment (step S105). At step S105, the control unit 64 reads the condition information 63a from the storage unit 63, and the initialization processor 64c uses the read condition information 63a to determine whether initialization of the image rotation angle is necessary.

Specifically, the condition information 63a includes a threshold concerning the capsule position information, a threshold concerning the capsule direction information, a threshold concerning the magnetic-field direction information, and a threshold concerning a correlation coefficient for images chronologically successive. The initialization processor 64c compares the respective thresholds in the condition information 63a with the capsule position information, the capsule direction information, and the magnetic-field direction information, that are acquired at step S104. The initialization processor 64c calculates correlation coefficients between successive in-vivo images by a known correlation function calculation, and compares the calculated correlation coefficients with the thresholds in the condition information 63a. In addition, the initialization processor 64c confirms whether an image signal of an in-vivo image is acquired from the receiving device 3, and further confirms whether the input unit 61 inputs the instruction information of an instruction for the initialization process on the image rotation angle. The initialization processor 64c determines whether a predetermined event concerning the capsule endoscope 2 occurs based on a result of comparing the various types of information with the thresholds, a result of acquiring an image signal, or the instruction information from the input unit 61. When the initialization processor 64c determines that the predetermined event concerning the capsule endoscope 2 occurs, the initialization processor 64c determines that it is necessary to perform the initialization process on the image rotation angle.

The predetermined event determined by the initialization processor 64c includes a first event that the magnetic guiding device 4 performs magnetic guidance in which the direction of the capsule endoscope 2 is changed by 90 degrees or more in a period where the capsule endoscope 2 takes one frame of in-vivo image; a second event that acquisition of in-vivo images stops; a third event that at least one of the position and the direction of the capsule endoscope 2 in the subject changes rapidly; a fourth event that a target position and a target direction in which the magnetic-field generator 41 applies a magnetic field largely are different from the capsule position information and the capsule direction information detected by the position detecting device 5 by a set value or more; a fifth event that the user manually issues a request for initialization process on the image rotation angle; and a sixth event that two chronologically-successive in-vivo images are largely different from each other (for example, the correlation coefficient of the successive two images is significantly low). For example, the third event from those events occurs when the capsule endoscope 2 in the subject moves between two different internal organs (for example, moves from the esophagus to the stomach or from the stomach to the duodenum) or rolls over the folds of the inner wall of the internal organ.

When the control unit 64 determines that initialization of an image rotation angle is necessary based on a result of the process performed by the initialization processor 64c (YES at step S105), the control unit 64 performs the initialization process on the image rotation angle by controlling the magnetic guiding device 4 to apply a magnetic field in the reference direction to the magnet 29 of the capsule endoscope 2 in the subject (step S106) and performs the rotation correction on subsequent in-vivo images based on the image whose image rotation angle is initialized in the initialization process (step S107).

At step S107, using the capsule position information, the capsule-direction information, and the magnetic-field direction information corresponding to the image (reference image) whose image rotation angle is initialized by the initialization processor 64c and the capsule position information, the capsule-direction information, and the magnetic-field direction information corresponding to the in-vivo image subsequent to the reference image, the image corrector 64b calculates the image rotation angle θ formed by the reference image and the subsequent in-vivo image. The image corrector 64b performs the rotation correction on the subsequent in-vivo image such that the calculated image rotation angle θ is 0. In this case, the image corrector 64b performs an interpolation process as necessary using data of each pixel forming the subsequent in-vivo image, and generates an in-vivo image on which rotation correction by the image rotation angle θ is performed in a direction such that the image plane direction of the reference image coincide with the image plane direction of the subsequent in-vivo image.

Subsequently, the control unit 64 causes the display unit 62 to display the in-vivo image on which the rotation correction is performed at step S107 (step S108). In this case, the control unit 64 causes the display unit 62 to display the in-vivo image on which the rotation correction is performed and, at the same time, the capsule position information, the capsule direction information, the magnetic-field intensity information, and the magnetic-field direction information corresponding to the in-vivo image. Thereafter, the control unit 64 determines whether the process is complete (step S109). When the process is not complete (NO at step S109), the control unit 64 goes back to step S102 and repeats the process procedure from step S102. In contrast, when the control unit 64 determines that the process is complete based on, for example, that the magnetic guidance of the capsule endoscope 2 is complete (YES at step S109), and completes the process.

At step S102, when the control unit 64 transmits information of an instruction for transmitting an image signal to the receiving device 3 but cannot acquire an image signal of an in-vivo image from the receiving device 3, the control unit 64 determines that no in-vivo image is acquired (NO at step S102). In this case, the user performs a process for, for example, adjusting the position of the bed on which the subject is laid, leading to a state where the receiving device 3 is ready to receive an in-vivo image from the capsule endoscope 2 in the subject, and the control unit 64 acquires an image signal of an in-vivo image from the receiving device 3 (step S103). Thereafter, the control unit 64 goes to step S104. When the control unit 64 determines that initialization of the image rotation angle is unnecessary at step S105 (NO at step S105), the control unit 64 goes to step S107 without performing the initialization process on the image rotation angle at step S106.

Figure 6:
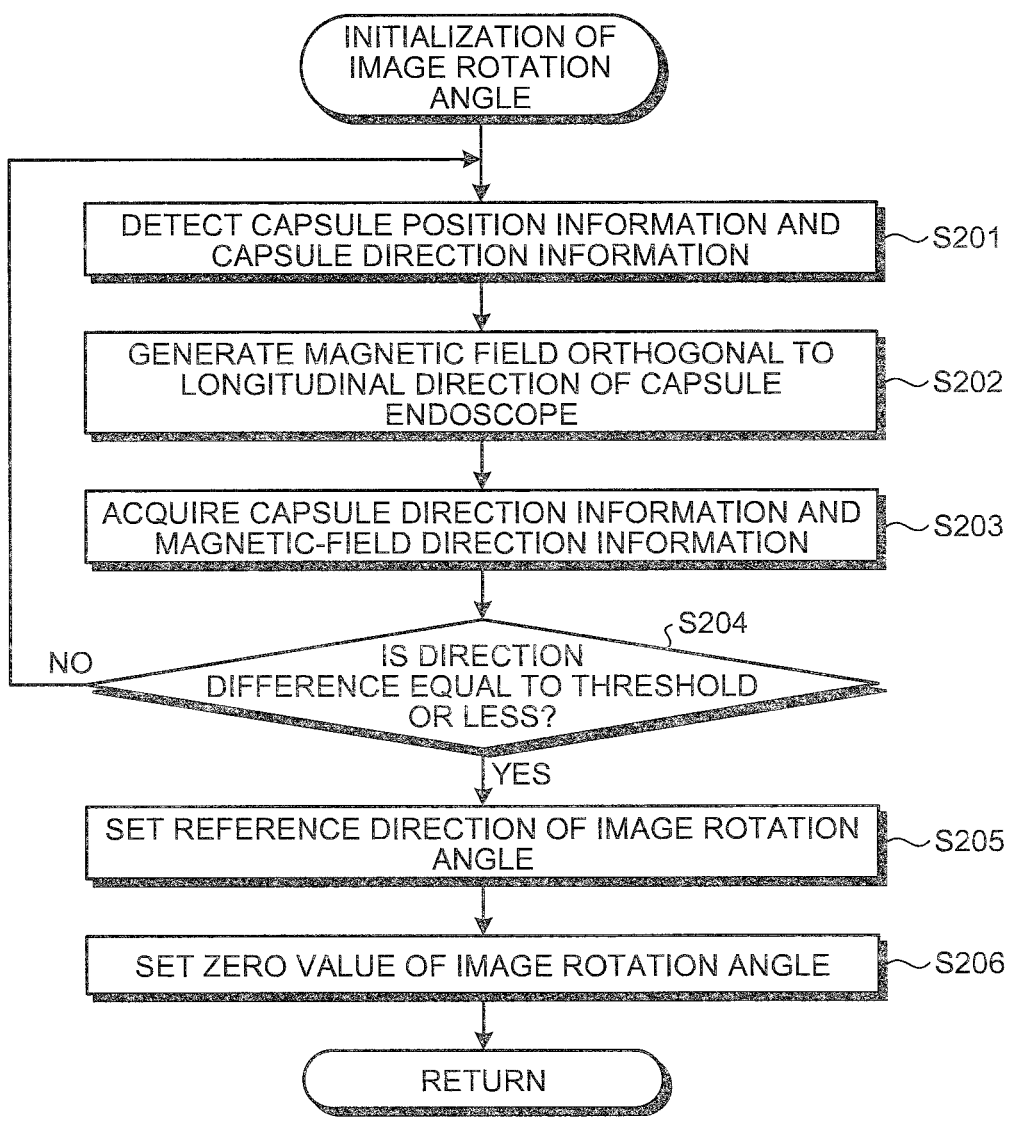
FIG. 6 is a flowchart illustrating a process procedure of the control unit performed when initializing an image rotation angle.

Subsequently, the initialization process on the image rotation angle at step S106 is explained. FIG. 6 is a flowchart illustrating a process procedure of the control unit 64 performed when initializing an image rotation angle. The control unit 64 that determines that initialization of the image rotation angle is necessary at step S105 causes the position detecting device 5 to detect the capsule position information and the capsule position information as illustrated in FIG. 6 (step S201). In this case, the control unit 64 controls the position detection controller 55 to calculate the capsule position information and the capsule direction information at the current moment. The control unit 64 then controls the position detection controller 55 to transmit the calculated capsule position information and the capsule direction information to the magnetic-field controller 44.

Subsequently, the control unit 64 causes the magnetic guiding device 4 to generate a magnetic field orthogonal to the longitudinal direction of the capsule endoscope 2 (step S202). At step S202, the control unit 64 controls the magnetic-field controller 44 to cause the magnetic-field generator 41 to emit a magnetic field in the reference direction. In this case, the magnetic-field controller 44 recognizes the current position of the capsule endoscope 2 and the longitudinal direction of the capsule endoscope 2 in the subject based on the capsule position information and the capsule direction information acquired from the position detection controller 55. The longitudinal direction of the capsule endoscope 2 is the direction of the longitudinal axis c of the capsule-shaped casing 21 (see FIG. 3). The magnetic-field controller 44 controls the magnetic-field generator 41 to generate a magnetic field in the reference direction, i.e., a magnetic field with a magnetization direction in the direction orthogonal to the longitudinal axis c (the radial direction of the capsule-shaped casing 21) at the current position of the capsule endoscope 2. In this case, the reference direction of the magnetic field is the direction orthogonal to the longitudinal direction of the capsule endoscope 2.

The capsule endoscope 2 to which a magnetic field in the reference direction is applied is magnetically guided such that the reference direction of the magnetic field and the magnetization direction of the magnet 29 coincide with each other due to the effect of the magnet 29 that moves following the magnetic field in the reference direction. Consequently, the magnet 29 is magnetized in the reference direction of the magnetic field.

Thereafter, the control unit 64 acquires the capsule direction information and the magnetic-field direction information at the current moment (time at which the magnetic field in the reference direction is applied to the capsule endoscope 2) from the magnetic-field controller 44 (step S203). At step S203, the control unit 64 controls the position direction controller 55 to calculate the capsule direction information at the time when the magnetic field in the reference direction is applied to the capsule endoscope 2. The control unit 64 controls the position detection controller 55 to transmit the capsule direction information to the magnetic-field controller 44. The control unit 64 controls the magnetic-field controller 44 to acquire the magnetic-field information representing the reference direction of the magnetic field and the capsule direction information at the time when the magnetic field in the reference direction is applied to the capsule endoscope 2.

Subsequently, the control unit 64 calculates a direction difference based on the magnetic-field direction information and the capsule direction information acquired at step S203, and determines whether the calculated direction difference is equal to a threshold or less (step S204). At step S204, the magnetic field direction information is information representing the reference direction (the radial direction of the capsule-shaped casing 21) of the magnetic field applied to the magnet 29 in the capsule endoscope 2. The capsule direction information is information representing the direction of the capsule endoscope 2 (specifically, the direction of the longitudinal axis c and the direction of the radial direction axis a illustrated in FIG. 3) at the time when the magnetic field in the reference direction is applied to the magnet 29 in the capsule endoscope 2. The control unit 64 calculates a direction difference that is a difference between the reference direction of the magnetic field and the direction of the radial direction axis a of the capsule endoscope 2 at the current moment. The reference direction of the magnetic field and the direction of the radial direction axis a coincide with each other when the magnet 29 in the capsule endoscope 2 is magnetized in the reference direction following the magnetic field in the reference direction. When the direction difference between the reference direction of the magnetic field and the direction of the radial direction axis a is larger than the predetermined threshold (NO at step S204), the control unit 64 recognizes that the difference between the reference direction of the magnetic field and the direction of the radial direction axis a of the capsule endoscope 2 is large (i.e., the magnet 29 is not magnetized in the reference direction of the magnet field), goes back to step S201, and repeats the process procedure from step S201.

In contrast, when the direction difference between the reference direction of the magnetic field and the direction of the radial direction axis a is equal to the predetermined threshold or less (YES at step S204), the control unit 64 recognizes that the reference direction of the magnetic field and the direction of the radial direction axis a of the capsule endoscope 2 coincide with each other (i.e., the magnet 29 is magnetized in the reference direction of the magnetic field). In this case, the control unit 64 sets the reference direction D1 of the image rotation angle (step S205).

At step S205, the initialization processor 64c acquires from the magnetic-field controller 44 the magnetic-field direction information that is to be associated with the image (reference image) taken by the imaging device 24 when the magnet 29 in the capsule endoscope 2 is magnetized in the reference direction of the magnetic field, and acquires an image plane direction of the reference image based on the acquired magnetic-field direction information. The image plane information of the reference image (for example, an in-vivo image) is relatively fixed with respect to the magnetization direction of the magnet 29 (for example, the direction of the radial direction axis a of the capsule endoscope 2) and is calculated based on the reference direction of the magnetic field that coincides with the magnetization direction. The initialization processor 64c sets the image plane direction of the reference image acquired as described above as the reference direction D1 of the image rotation angle.

Subsequently, the control unit 64 sets 0 of the image rotation angle based on the reference direction D1 of the image rotation angle (step S206) and thereafter returns to step S106. At step S206, the initialization processor 64c defines the image rotation angle θ formed by the reference direction D1 set at step S205 and the image plane direction of the in-vivo image subsequent to the reference image, and sets the image rotation angle θ of the in-vivo image whose image plane direction coincides with the reference direction D1 to 0.

The process procedure to achieve the initialization process on the image rotation angle at step S101 (see FIG. 5) is similar to that from step S201 to step S206. In other words, the control unit 64 achieves the initialization process on the image rotation angle at step S101 by performing the process procedure similar to that from step S201 to step S206, and thereafter returns to step S101.

Figure 7:
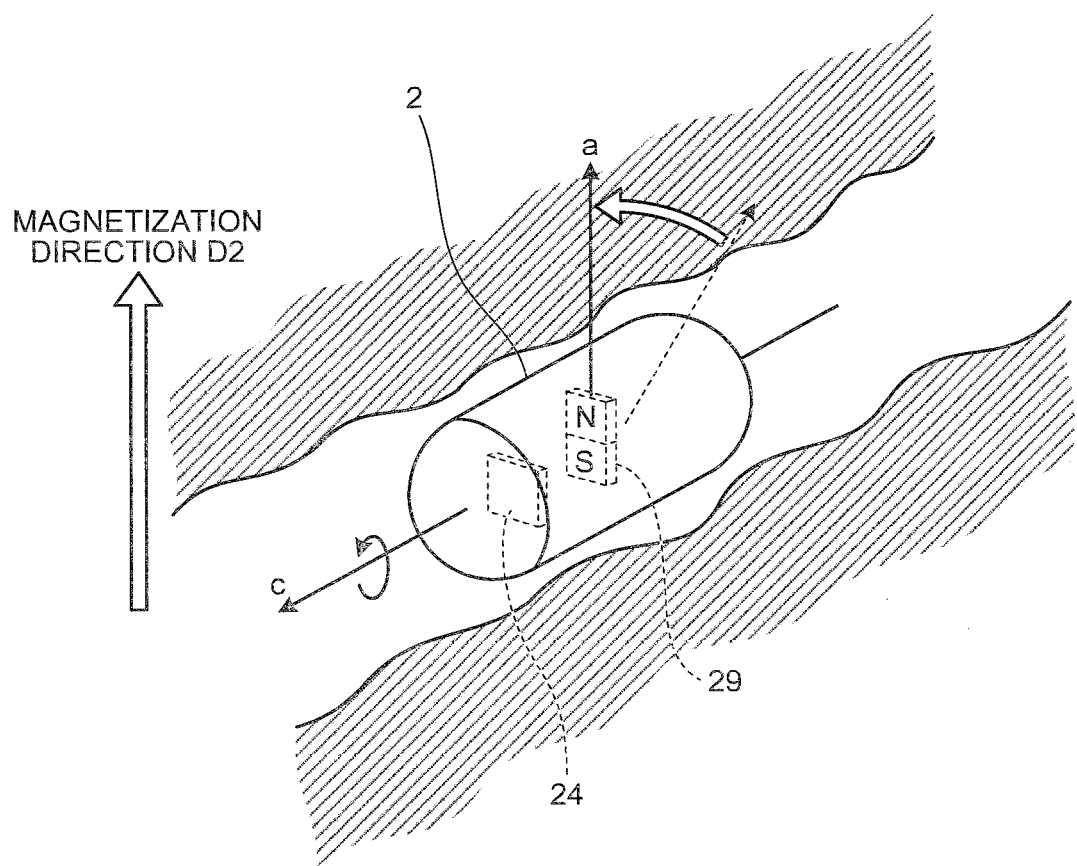
FIG. 7 is a schematic diagram illustrating a state in which a magnetic field in a reference direction is applied to the capsule endoscope in the subject.
Figure 8:
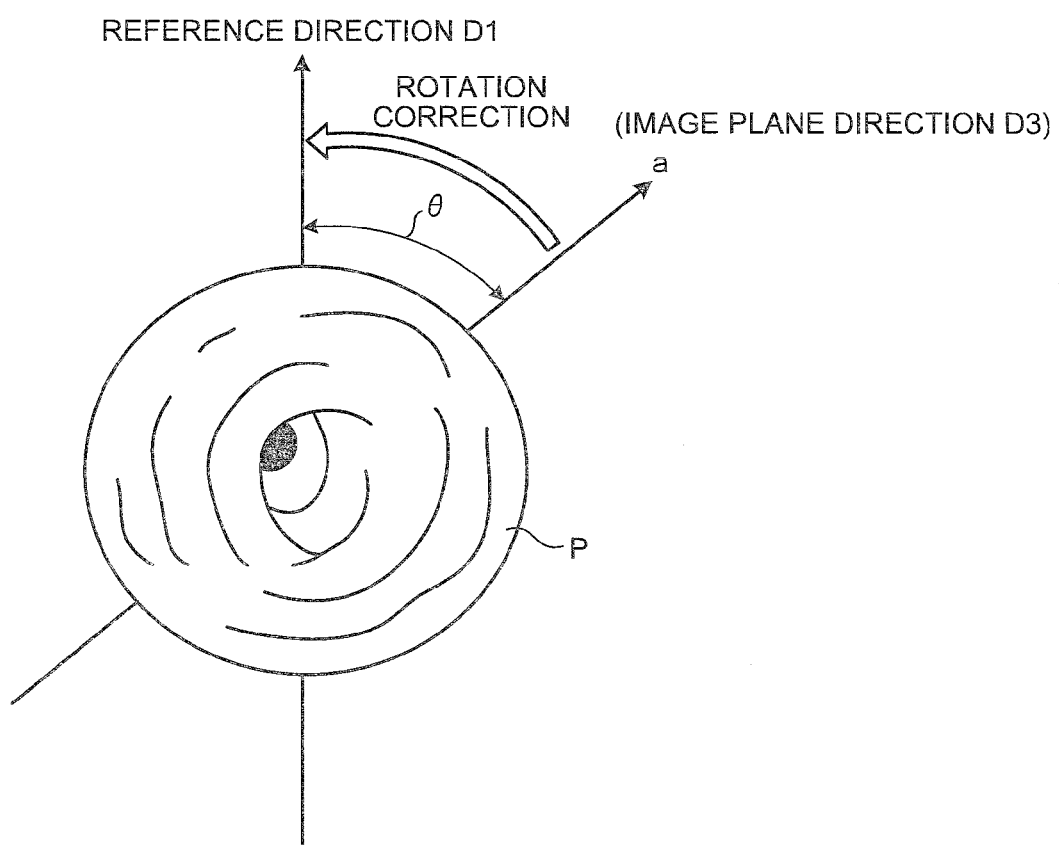
FIG. 8 is a schematic diagram illustrating a state in which rotation correction is performed on an in-vivo image.

Subsequently, the initialization process on the image rotation angle and the rotation correcting process on the in-vivo image are specifically explained. FIG. 7 is a schematic diagram illustrating a state where a magnetic filed in the reference direction is applied to the capsule endoscope 2 in the subject. FIG. 8 is a schematic diagram illustrating a state where rotation correction is performed on an in-vivo image.

When the initialization processor 64c performs the initialization process on the image rotation angle, the position detecting device 5 detects the current position and the current direction of the capsule endoscope 2 in the subject under the control of the control unit 64, and sends a result of the detection to the magnetic guiding device 4. The magnetic guiding device 4 generates a magnetic field in the reference direction orthogonal to the current direction (the longitudinal direction) of the capsule endoscope 2. Specifically, the magnetic guiding device 4 applies a magnetic field in the reference direction orthogonal to the longitudinal axis c of the capsule endoscope 2 to the magnet 29 of the capsule endoscope 2 in the subject.

The magnet 29 to which the magnetic field in the reference direction is applied takes the rotation movement on the longitudinal axis c following the magnetic field in the reference direction as illustrated in FIG. 7, so that the magnetization direction is changed from the direction represented by the dotted-line arrow to the direction represented by the solid-line arrow. In this case, the magnetization direction of the magnet 29 (the direction in the radial direction axis a of the capsule endoscope 2) finally coincides with the reference direction of the magnetic field (the magnetic-field direction D2 illustrated in FIG. 7). The imaging device 24 rotates on the longitudinal axis c following the rotation movement of the magnet 29, so that the reference plane direction of the light receiving surface and the magnetic-field direction D2 coincide with each other.

The initialization processor 64c initializes the image rotation angle of the in-vivo image taken by the imaging device 24 (an example of reference image) in the state where the reference plane direction of the light receiving surface and the magnetic-field direction D2 (the reference direction of the magnetic field) coincide with each other. Specifically, based on the magnetic-field direction D2, which coincides with the image plane direction of the in-vivo image, the initialization processor 64c sets the image plane direction of the in-vivo image to the reference direction D1 of the image rotation angle, and sets the image rotation angle θ of the in-vivo image whose image plane direction coincides with the reference direction D1 to 0. In this case, the reference direction D1 of the image rotation angle set by the initialization processor 64c represents an upper direction of the in-vivo image taken by the imaging device 24 and coincides with the magnetic-field direction D2 and the radial direction axis a illustrated in FIG. 7.

As illustrated in FIG. 8, the image corrector 64b calculates the image rotation angle θ formed by the reference direction D1 set by the initialization processor 64c and the image plane direction D3 of an in-vivo image P, and performs the rotation correction on the in-vivo image P such that the calculated image rotation angle θ is 0. In this case, using data on each pixel constituting the in-vivo image P, the image corrector 64b performs the interpolation process as required, and generates an in-vivo image on which rotation correction is performed by the image rotation angle θ in a direction such that the reference direction D1 and the image plane direction D3 of the in-vivo image P coincide with each other.

The in-vivo image P is an in-vivo image subsequent to the in-vivo image (i.e., the reference image) in which the reference direction D1 is set by the initialization processor 64c. The image plane direction of the in-vivo image P coincides with the direction of the radial direction axis a of the capsule endoscope 2 as the reference plane direction of the light receiving plane of the imaging device 24.

The control unit 64 causes the display unit 62 to display the in-vivo image on which the rotation correction is performed by the image corrector 64b. In this case, the control unit 64 causes the display unit 62 to display the in-vivo image in the state where the reference plane direction of the display unit 62 (for example, the upper direction of the display screen) and the image plane direction D3 of the in-vivo image on which the rotation correction is performed (i.e., the reference direction D1) coincide with each other. Thus, the control unit 64 can, for example, make the upper, lower, right, and left directions of the display screen of the display unit 62 coincide respectively with the upper, lower, right, and left directions of the in-vivo image with high accuracy. Accordingly, in-vivo images of the subject can be sequentially displayed on the display unit 62 such that they can be easily observed and magnetic guidance of the capsule endoscope 2 in the subject, which is performed with reference to in-vivo images displayed on the display unit 62, can be easily operated.

As explained above, the embodiment of the present invention employs the configuration in which the capsule medical device including in the capsule-shaped casing the imaging device to take an in-vivo image of a subject and a magnet with a magnetization direction relatively fixed with respect to the imaging device is introduced into a subject, the magnetic guiding device that magnetically guides the capsule medical device in the subject is controlled to apply a magnetic field in the reference direction to the magnet in the capsule medical device, the rotation angle of the image taken by the imaging device when the magnet is magnetized in the reference direction according to the applied magnetic field is initialized, rotation correction is performed on subsequent images based on the image whose rotation angle is initialized, and in-vivo images of the subject on which the rotation correction is performed are sequentially displayed on the display unit. Thus, the magnetization direction of the magnet in the capsule medical device can be controlled with the magnetic field in the reference direction, so that the reference direction of the image rotation angle can be set with high accuracy. As a result, a capsule guiding system and a capsule guiding method in which initialization on the image rotation angle of an image taken, using an imaging device, by a capsule medical device that is magnetically guided can be performed with high accuracy can be achieved.

Furthermore, the configuration is employed in which it is determined whether it is necessary to initialize the image rotation angle of the in-vivo image taken, using the imaging device, by the capsule medical device in the subject. When it is determined that the initialization is necessary, a magnetic field in the reference direction is applied by the magnetic guiding device to the magnet in the capsule medical device positioned in the subject, and the rotation angle of the image that is taken by the imaging device when the magnet is magnetized in the reference direction according to the applied magnetic field is initialized. Thus, even after the capsule medical device is introduced into the subject, the magnetization direction of the magnet in the capsule medical device can be controlled with a magnetic field in the reference direction. Therefore, if an event that requires that initialization of the image rotation angle be performed occurs in the capsule medical device in the subject, initialization on the image rotation angle can be performed depending on the event. As a result, in the period from the capsule medical device is introduced into the subject until it is excreted to the outside of the subject, the accuracy in initialization of the image rotation angle can be maintained at a high level and reference plane directions of in-vivo images to be sequentially displayed on the display unit can be made coincide with high accuracy by the rotation correction on images.

Furthermore, because in-vivo images are sequentially displayed on the display unit in a state that the reference plane direction of the display unit and the reference plane direction of each in-vivo image are made coincide with each other, the upper, lower, right, and left directions of each in-vivo image, which are defined by the reference plane direction of the light receiving surface of the imaging device, are made coincide respectively with the upper, lower, right, and left directions of the display screen of the display unit with high accuracy. Accordingly, in-vivo images of the subject can be sequentially displayed on the display unit such that they can be easily observed, and magnetic guidance of the capsule medical device in the subject, which is performed with reference to the in-vivo images displayed on the display unit, can be easily operated.

In the embodiment of the present invention, the reference direction of the magnetic field applied to the magnet 29 in the capsule endoscope 2 is the direction orthogonal to the longitudinal axis c of the capsule-shaped casing 21, however, the invention is not limited to this. The reference direction of the magnetic field may be a specific direction in the above-described absolute coordinate system. In this case, the image rotation angle can be initialized by making the absolute specific direction in the absolute coordinate system and the reference direction of the image rotation angle coincide with each other. As a result, the rotation correcting process for making the reference direction of the image rotation angle and the image plane direction of the in-vivo image coincide with each other can be easily performed.

In the embodiment of the present invention, the magnetization direction of the magnet 29 and the upper direction of the imaging device 24 are relatively fixed and the upper direction of the imaging device 24 is set to the reference plane direction of the in-vivo image, however, the invention is not limited to this. As long as the magnetization direction of the magnet 29 and the reference plane direction of the light receiving surface of the imaging device 24 are relatively fixed, the reference plane direction of the light receiving surface of the imaging device 24, i.e., the image plane direction of the in-vivo image may be a desired plane direction other than the upper direction.

Furthermore, in the embodiment of the present invention, the capsule guiding system for magnetically guiding the capsule endoscope 2 that takes an in-vivo image of a subject is illustrated, however, the invention is not limited to this. As long as the imaging device and the magnet are fixedly arranged in the capsule-shaped casing in the state where the reference plane direction of the imaging device and the magnetization direction of the magnet are relatively fixed, the capsule medical device may be a capsule pH measuring device that measures pH of a human body, a capsule medication applying device having a function of applying or injecting a medication to the body, or a capsule sampling device that samples a substance in a body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule guiding system comprising:
   a capsule medical device including in a capsule casing an imaging device configured to take an in-vivo image of a subject and a magnet with a magnetization direction that is relatively fixed with respect to the imaging device;
   a magnetic guiding device configured to apply a magnetic field to the magnet of the capsule medical device introduced into the subject and to guide the capsule medical device with the magnetic field;
   a display unit configured to display the in-vivo image of the subject taken by the imaging device; and
   a control unit configured to cause the magnetic guiding device to apply a magnetic field in a reference direction to the magnet, configured to initialize a rotation angle of an image taken by the imaging device when the magnetization direction of the magnet is oriented to the reference direction following the magnetic field in the reference direction, configured to perform, referring to the image, rotation correction on subsequent in-vivo images, and configured to cause the display unit to sequentially display the in-vivo images on which the rotation correction is performed, wherein the control unit is configured to determine whether performing initialization of the rotation angle is necessary, and upon determination that performing the initialization is necessary, the control unit causes the magnetic guiding device to apply the magnetic field in the reference direction to the magnet and initializes the rotation angle of the image taken by the imaging device when the magnetization direction of the magnet is oriented to the reference direction following the magnetic field in the reference direction.

2. The capsule guiding system according claim 1, further comprising a storage unit configured to store condition information on necessity of the initialization of the rotation angle, wherein the control unit is configured to determine whether performing the initialization of the rotation angle is necessary based on the condition information.

3. The capsule guiding system according to claim 2, further comprising a detecting device configured to detect position information and direction information on the capsule medical device in the subject, wherein
   the condition information includes at least a threshold concerning the position or direction of the capsule medical device, and
   the control unit is configured to perform a comparing process to compare the position information or the direction information with the threshold and to determine whether performing the initialization of the rotation angle is necessary on the basis of the comparing process.

4. The capsule guiding system according to claim 3, wherein the condition information includes information on an amount of change in the direction of the capsule medical device in a period in which the imaging device takes one frame of in-vivo image.

5. The capsule guiding system according to claim 3, wherein
   the control unit is configured to determine whether an image signal of the in-vivo image taken by the imaging device is acquired, and
   upon determination that the image signal is not acquired, the control unit determines that performing the initialization of the rotation angle is necessary.

6. The capsule guiding system according to claim 3, wherein the condition information includes information on a change in at least any one of the position and direction of the capsule medical device in the subject.

7. The capsule guiding system according to claim 3, wherein the condition information includes information on a difference between a target position in which the magnetic guiding device applies a magnetic field and the position of the capsule medical device.

8. The capsule guiding system according to claim 3, wherein the condition information includes information on a difference between a target direction in which the magnetic guiding device applies a magnetic field and the direction of the capsule medical device.

9. The capsule guiding system according to claim 3, wherein the condition information includes information on a correlation between two subsequent images taken by the imaging device chronologically.

10. The capsule guiding system according to claim 1, wherein the control unit is configured to make a plane direction of the in-vivo image corresponding to the reference direction coincide with a reference plane direction of the display unit by the rotation correction and to cause the display unit to display the in-vivo image.

11. A capsule guiding method for magnetically guiding a capsule medical device that is introduced into a subject and sequentially takes in-vivo images chronologically, the capsule guiding method comprising:

acquiring information on magnetic guidance of the capsule medical device;

determining whether initialization of a rotation angle of an image taken by the capsule medical device is necessary based on the information on the magnetic guidance of the capsule medical device, which is acquired at the acquiring, and condition information previously set;

performing, when it is determined that the initialization of the rotation angle of the image is necessary at the determining, an initialization process on the rotation angle of the image;

performing rotation correction on subsequent images taken by the capsule medical device referring to the image whose rotation angle is initialized at the initialization process step; and displaying the subsequent images on which the rotation correction is performed at the rotation correction.

12. The capsule guiding method according to claim 11, wherein the initialization process includes detecting position information and direction information on the capsule medical device in the subject;

generating a magnetic field orthogonal to a longitudinal direction of the capsule medical device based on the direction information at a current position of the capsule medical device based on the position information;

acquiring direction information on the magnetic field generated at the generating and direction information on the capsule medical device to which the magnetic field is applied;

determining whether a direction difference between the direction information on the magnetic field and the direction information on the capsule medical device acquired at the acquiring is equal to a threshold or less;

setting, when the direction difference is equal to the threshold or less, the reference direction of the rotation angle of the image based on the direction information on the magnetic field; and setting the rotation angle of the image to zero based on the reference direction set at the reference direction setting.

\* \* \* \* \*